(12) United States Patent
Kishore Kumar et al.

(10) Patent No.: US 12,374,132 B2
(45) Date of Patent: Jul. 29, 2025

(54) SYSTEMS AND METHODS FOR PREDICTING PATIENT RESPONSES

(71) Applicant: Sanofi, Paris (FR)

(72) Inventors: Vardaan Kishore Kumar, Jersey City, NJ (US); Qi Tang, Hopewell, NJ (US)

(73) Assignee: Sanofi, Paris (FR)

(*) Notice: Subject to any disclaimer, the term of this patent is extended or adjusted under 35 U.S.C. 154(b) by 423 days.

(21) Appl. No.: 17/796,437

(22) PCT Filed: Feb. 4, 2021

(86) PCT No.: PCT/US2021/016620
§ 371 (c)(1),
(2) Date: Jul. 29, 2022

(87) PCT Pub. No.: WO2021/158794
PCT Pub. Date: Aug. 12, 2021

(65) Prior Publication Data
US 2023/0343117 A1    Oct. 26, 2023

Related U.S. Application Data

(60) Provisional application No. 62/971,630, filed on Feb. 7, 2020.

(30) Foreign Application Priority Data

Jul. 2, 2020 (EP) ..................... 20315338

(51) Int. Cl.
*G06K 9/00* (2022.01)
*G06T 7/00* (2017.01)
(Continued)

(52) U.S. Cl.
CPC .......... *G06V 20/698* (2022.01); *G06T 7/0012* (2013.01); *G06T 7/11* (2017.01);
(Continued)

(58) Field of Classification Search
None
See application file for complete search history.

(56) References Cited

U.S. PATENT DOCUMENTS

2019/0156159 A1    5/2019 Kopparapu
2020/0027545 A1    1/2020 Xie et al.

FOREIGN PATENT DOCUMENTS

CN    108648182 A    10/2018
JP    2017-516992 A    6/2017
(Continued)

OTHER PUBLICATIONS

Ilse et al., "Attention-based Deep Multiple Instance Learning," Proceedings of the 35th International Conference on Machine Learning, 2018, 16 pages.
(Continued)

*Primary Examiner* — Wei Wen Yang
(74) *Attorney, Agent, or Firm* — Fish & Richardson P.C.

(57) ABSTRACT

Data processing systems for predicting one or more responses to a chemical substance based on biological images. At least some of the data processing systems include at least one processor configured to execute at least one artificial neural network trained to predict one or more responses to a chemical substance based on biological images. When the at least one processor is executing computer-executable instructions, the at least one processor is configured to carry out operations including processing spatially arranged image tile data through one or more data structures storing one or more portions of executable logic included in the artificial neural network to determine one or more responses of a patient to the chemical substance.

20 Claims, 8 Drawing Sheets

(51) Int. Cl.
　　　*G06T 7/11*　　　(2017.01)
　　　*G06V 10/82*　　(2022.01)
　　　*G06V 20/69*　　(2022.01)

(52) U.S. Cl.
　　　CPC ............ *G06V 10/82* (2022.01); *G06V 20/695* (2022.01); *G06T 2207/20021* (2013.01); *G06T 2207/20084* (2013.01); *G06T 2207/30004* (2013.01)

(56) References Cited

FOREIGN PATENT DOCUMENTS

| WO | WO 2008/124138 | | 10/2008 | |
| WO | WO 2012/038068 | | 3/2012 | |
| WO | WO 2015/177268 | A1 | 11/2015 | |
| WO | WO 2018/221625 | A1 | 12/2018 | |
| WO | WO 2019/084697 | | 5/2019 | |
| WO | WO 2019/226270 | A1 | 11/2019 | |
| WO | WO-2020198380 | A1 * | 10/2020 | ....... G06F 18/24143 |

OTHER PUBLICATIONS

International Preliminary Report on Patentability in International Appln. No. PCT/US2021/016620, mailed on Aug. 18, 2022, 8 pages.

International Search Report and Written Opinion in International Appln. No. PCT/US2021/016620, mailed on May 25, 2021, 9 pages.

Silva et al., "PD-L1 immunostaining scoring for non-small cell lung cancer based on immunosurveillance parameters," PLOS One, Jun. 6, 2018, 13(6):e0196464.

He et al., "Deep Residual Learning for Image Recognition," CoRR, Submitted on Dec. 10, 2015, arXiv:1512.03385v1, 12 pages.

Simonyan et al., "Very Deep Convolutional Networks for Large-Scale Image Recognition," CoRR, Submitted on Sep. 4, 2014, arXiv:1409.1556v6, 14 pages.

* cited by examiner

SYSTEMS AND METHODS FOR PREDICTING PATIENT RESPONSES

CROSS-REFERENCE TO RELATED APPLICATIONS

This application is a National Stage entry of PCT/US2021/016620, filed on Feb. 4, 2021, which claims priority from European Patent Application No. 20315338.2, filed Jul. 2, 2020, and U.S. Provisional Patent Application No. 62/971,630, filed Feb. 7, 2020, the contents and disclosures of which are incorporated herein by reference in their entireties.

TECHNICAL FIELD

This disclosure generally relates to systems and methods that predict patient responses to chemical compounds, such as pharmaceutical drugs.

BACKGROUND

Clinical trials are typically conducted to collect data regarding the safety and efficacy of pharmaceutical drugs. Generally, these trials involve one or more phases that determine whether a drug can be sold in a consumer market. For example, a clinical trial may include three phases. In the first phase, the drugs are tested on a relatively small number of paid volunteers (e.g., 20 to 100 volunteers) to determine the effects of the drug, including absorption, metabolization, excretion, and so forth. This phase can take several months to complete and approximately 70% of experimental drugs pass the first phase. In the second phase, the experimental drugs are tested on several hundred patients that meet one or more inclusion criteria. One group of patients receive the experimental drugs while another group receives a placebo or a standard treatment. About one-third of experimental drugs complete both phase one and phase two of testing. During the third phase, the drugs are tested on several hundred to several thousands of patients (or more). This phase tends to be the most costly of all phases, and approximately 70% of drugs that enter phase three may successfully complete the phase.

SUMMARY

In at least one aspect of the present disclosure, a data processing system is provided. The data processing system includes a computer-readable memory comprising computer-executable instructions; and at least one processor configured to execute at least one artificial neural network trained to predict one or more responses to a chemical substance based on biological images. When the at least one processor is executing the computer-executable instructions, the at least one processor is configured to carry out one or more operations. The one or more operations include receiving spatially arranged image data representing a plurality of biological images of a patient. The one or more operations include generating, for each biological image of the plurality of biological images, spatially arranged image tile data representing a plurality of image tiles, in which each image tile of the plurality of image tiles includes a discrete portion of the biological image. The one or more operations include processing the spatially arranged image tile data through one or more data structures storing one or more portions of executable logic included in the artificial neural network to: classify, for each image of the plurality of images, the image as representing or not representing abnormal tissue by analyzing the plurality of image tiles corresponding to the image; for each image classified as representing abnormal tissue, classify the image as indicating or not indicating that the patient will respond to the chemical substance by analyzing the plurality of image tiles corresponding to the image; and determine, based on the images classified as indicating or not indicating that the patient will respond to the chemical substance, one or more responses of the patient to the chemical substance.

The artificial neural network can include at least one convolutional layer and at least one fully connected layer.

Classifying the image as representing or not representing abnormal tissue can include assigning an abnormality weight to each image tile of the plurality of image tiles corresponding to the image. The abnormality weight can indicate a predictive power of the image tile corresponding to the abnormality weight for classifying the image corresponding to the image tile as representing or not representing abnormal tissue. Classifying the image as indicating or not indicating that the patient will respond to the chemical substance can include assigning a response weight to each image tile of the plurality of image tiles corresponding to the image. The response weight can indicate a predictive power of the image tile corresponding to the response weight for classifying the image corresponding to the image tile as indicating or not indicating that the patient will respond to the chemical substance.

The plurality of images can include a plurality of immunohistochemistry images. The abnormal tissue can include a cancerous tumor.

These and other aspects, features, and implementations can be expressed as methods, apparatus, systems, components, program products, means or steps for performing a function, and in other ways.

Implementations of the present disclosure can provide one or more of the following advantages. Image processing and machine learning techniques can be used to process image data to predict patient responses to a drug in such a manner that, when compared with traditional techniques, prediction accuracy is increased, computational efficiency is increased, and/or computational power requirements are decreased. When compared to traditional techniques, the predictions can account for an increased number of variables, which can increase the accuracy of the predictions. When compared with traditional techniques, interpretability of machine learning output and ease of convergence is increased.

These and other aspects, features, and implementations will become apparent from the following descriptions, including the claims.

DETAILED DESCRIPTION

Figure 1:
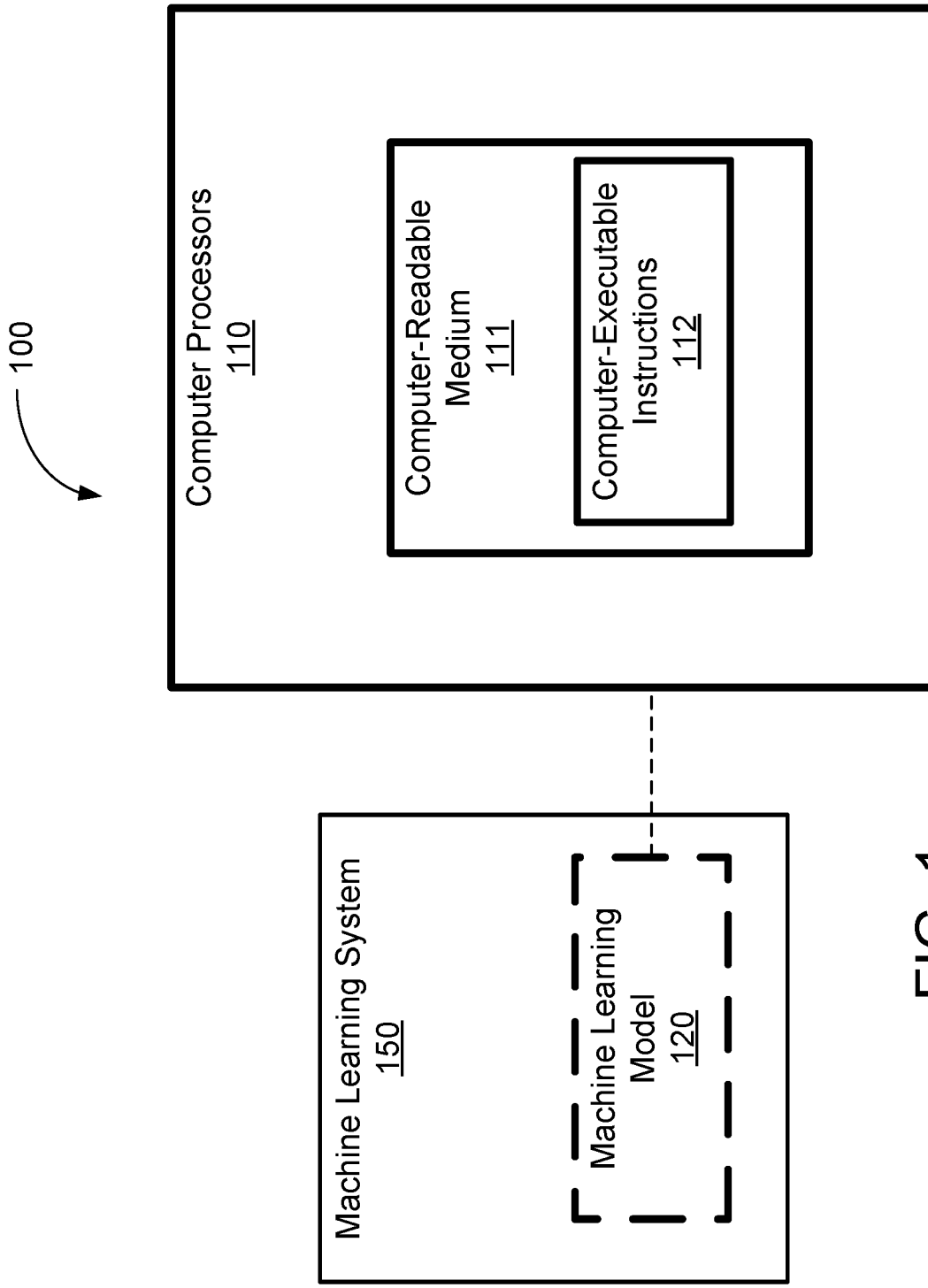
FIG. 1 is a diagram illustrating an example of a data processing system.

For clinical trials involving a given drug, selecting patients to be treated who may benefit from the treatment with manageable side effects can be important, especially in the fields of life threatening diseases, such as oncology. Due to recent advancements in medical imaging technology, medical images or biological images (for example, immunohistochemistry images) can be useful in predicting patient outcomes to an investigational treatment. However, traditional patient outcome predicting techniques typically extract only a few features from the biological images, such as proportional scores and histochemical scores (sometimes referred to as an "H-score"). As a result, the resulting patient response prediction accuracy can range from 20%-45%. Furthermore, using traditional machine learning techniques to predict patient responses to a given drug can be computationally unfeasible, as the biological images can have sizes of 2 gigabytes (or more) with dimensions of 50,000 pixels by 40,000 pixels (or more). That is, images of these size can require a machine learning model to estimate for billions (or more) of parameters.

Implementations of the present disclosure provide systems and methods for predicting patient responses that can be used to alleviate some or all of the aforementioned disadvantages. The system and methods described in the present disclosure can implement image processing techniques, and machine learning techniques, such that image data representing biological images can be processed in a more computationally efficient manner to predict patient responses to a drug with a higher degree of accuracy, when compared with traditional techniques. In some implementations, the machine learning techniques include multiple instance learning techniques that implement a two-step multi-classification method. In some implementations, the systems and methods described in this disclosure can receive data representing a plurality of biological images of a patient and generate image tiles (sometimes referred to herein as instances), in which each image tile represents a discrete portion of the biological image. Data representing each biological image can be processed with an artificial neural network (ANN) that can classify, for each image, as representing or not representing abnormal tissue (e.g., whether or not the image includes cancerous tumor cells) by analyzing the image tiles corresponding to the image. This can include assigning abnormality weights to each of the image tiles corresponding to the image, in which the abnormality weights reflect the predictive power of the image tile for predicting whether or not the image corresponding to the tile represents abnormal tissue. In some implementations, image data representing the images classified as representing abnormal tissue are further processed by the ANN to classify these images as indicating or not indicating that the patient will respond to a chemical substance (e.g., whether or not the images show that a chemical substance will reduce the cancerous tumor) by analyzing the corresponding image tiles. This can include assigning response weights to each of the image tiles corresponding to the image, in which the response weights reflect the predictive power of the image tile for predicting whether or not the image corresponding to the tile indicates that the patient will respond to a chemical substance. The per-image predictions can then be aggregated to determine if the patient will respond to the chemical substance.

The ANN can be trained to identify higher level features from the images that may affect the patient response prediction. For example, the ANN may learn to associate partially stained patterns of targeted proteins on a membrane of a tumor nest with poor patient responses because an active drug ingredient may not recognize the targeted protein to attack the tumor nest. Examples of patient response can include efficacy responses (such as, a reduction/change in the size of a cancerous tumor resulting from the patient undergoing an oncology drug treatment regimen), safety responses (such as adverse reactions, toxicity, and cardiovascular risks resulting from the patient undergoing an oncology drug treatment regimen), or both.

In the following description, for the purposes of explanation, numerous specific details are set forth in order to provide a thorough understanding of the present disclosure. It will be apparent, however, that the present disclosure may be practiced without these specific details. In other instances, well-known structures and devices are shown in block diagram form in order to avoid unnecessarily obscuring the present disclosure.

In the drawings, specific arrangements or orderings of schematic elements, such as those representing devices, modules, instruction blocks and data elements, are shown for ease of description. However, the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood that such element may represent one or multiple signal paths (e.g., a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described in this specification. Although headings are provided, data related to a particular heading, but not found in the section having that heading, may also be found elsewhere in this description.

FIG. 1 shows an example of a data processing system 100. Generally, the data processing system 100 is configured to process image data representing biological images of a patient to predict a patient response (for example, reduction in size of a cancerous tumor) for a given chemical substance (for example, a pharmaceutical drug). The system 100 includes computer processors 110. The computer processors 110 include computer-readable memory 111 and computer readable instructions 112. The system 100 also includes a machine learning system 150. The machine learning system 150 includes a machine learning model 120. The machine learning model 120 can be separate from or integrated with the computer processors 110.

The computer-readable medium 111 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In some implementations, the computer-readable medium 111 includes code-segment having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, graphic processing units, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code such as the computer-executable instructions 112 and configured to execute executable logic that includes the machine learning model 120.

The computer processors 110 are configured to receive image data representing a plurality of medical images of a patient. For example, the medical images of a patient can include one or more images of the results of immunohistochemically staining, which describes a process of selectively identifying proteins (e.g., antigens) in cells of a biological tissue section by exploiting the principle of antibodies binding specifically to antigens in biological tissue. The image data can be obtained through any of various techniques, such as wireless communications with databases, optical fiber communications, USB, CD-ROM, and so forth.

In some implementations, the computer processors 110 are configured to generate image tile data representing a plurality of image tiles in which each image tile includes a discrete portion of one of the biological images. For example, if a biological image includes dimensions of 4096×4096, the computer processors 110 can segment the image into 256 tiles, each having dimensions of 256×256.

The machine learning model 120 is capable of processing the image data to predict a patient response corresponding to a certain chemical substance (e.g., a pharmaceutical drug). For example, for a given oncology treatment drug regimen, the machine learning model 120 can predict an amount of reduction in the size of a cancerous tumor by analyzing the image tiles of the plurality of images. In some implementations, predicting the patient response includes assigning one or more weight values to the tiles, and labeling the images in accordance with the weight values. Predicting the patient response is discussed in more detail later with reference to FIGS. 2-5.

The machine learning system 150 is capable of applying machine learning techniques to train the machine learning model 120. As part of the training of the machine learning model 120, the machine learning system 150 forms a training set of input data by identifying a positive training set of input data items that have been determined to have the property in question, and, in some implementations, forms a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In one implementation, the machine learning system 150 applies dimensionality reduction (e.g., via linear discriminant analysis (LDA), principle component analysis (PCA), or the like) to reduce the amount of data in the feature vectors for the input data to a smaller, more representative set of data.

In some implementations, the machine learning system 150 uses supervised machine learning to train the machine learning models 120 with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—may be used in different implementations. The machine learning model 120, when applied to the feature vector extracted from the input data item, outputs an indication of whether the input data item has the property in question, such as a Boolean yes/no estimate, or a scalar value representing a probability.

In some implementations, a validation set is formed of additional input data, other than those in the training sets, which have already been determined to have or to lack the property in question. The machine learning system 150 applies the trained machine learning model 120 to the data of the validation set to quantify the accuracy of the machine learning model 120. Common metrics applied in accuracy measurement include: Precision=TP/(TP+FP) and Recall=TP/(TP+FN), where precision is how many the machine learning model correctly predicted (TP or true positives) out of the total it predicted (TP+FP or false positives), and recall is how many the machine learning model correctly predicted (TP) out of the total number of input data items that did have the property in question (TP+FN or false negatives). The F score (F-score=2*PR/(P+R)) unifies precision and recall into a single measure. In one implementation, the machine learning module iteratively re-trains the machine learning model until the occurrence of a stopping condition, such as the accuracy measurement indication that the model is sufficiently accurate, or a number of training rounds having taken place.

In some implementations, the machine learning model 120 is a convolutional neural network (CNN). A CNN can be configured based on a presumption that inputs to the CNN correspond to image pixel data for an image or other data that includes features at multiple spatial locations. For example, sets of inputs can form a multi-dimensional data structure, such as a tensor, that represent color features of an example digital image (e.g., a biological image of biological tissue). In some implementations, inputs to the CNN correspond to a variety of other types of data, such as data obtained from different devices and sensors, point cloud data, audio data that includes certain features or raw audio at each of multiple time steps, or various types of one-dimensional or multiple dimensional data. A convolutional layer of the CNN can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which CNN performs the computations can be based on specific properties for each layer of an example multi-layer neural network or deep neural network that supports deep neural net workloads. A deep neural network can include one or more convolutional towers (or layers) along with other computational layers. In particular, for computer vision applications, these convolutional towers often account for a large proportion of the inference calculations that are performed. Convolutional layers of a CNN can have sets of artificial neurons that are arranged in three dimensions—a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R,G,B. A convolutional layer of a CNN of the machine learning model 120 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the machine learning model 120 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The machine learning model 120 can then compute a dot product from the overlapped elements. For example, the machine learning model 120 can convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The machine learning model 120 can convolve each kernel over each input of an input volume. The machine learning model 120 can perform this convolution operation by, for example, moving (or sliding) each kernel over each input in the region.

The machine learning model 120 can move each kernel over inputs of the region based on a stride value for a given convolutional layer. For example, when the stride is set to 1, then the machine learning model 120 can move the kernels over the region one pixel (or input) at a time. Likewise, when the stride is 2, then the machine learning model 120 can move the kernels over the region two pixels at a time. Thus, kernels may be shifted based on a stride value for a layer and the machine learning model 120 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the machine learning model 120 can produce a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the CNN.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In some implementations, the spatial size of the output volume is computed as a function of the input volume size, W, using the formula $(W-F+2P)/S+1$. For example, an input tensor can represent a pixel input volume of size [227×227×3]. A convolutional layer of a CNN can have a spatial extent value of F=11, a stride value of S=4, and no zero-padding (P=0). Using the above formula and a layer kernel quantity of K=96, the machine learning model 120 performs computations for the layer that results in a convolutional layer output volume of size [55×55×96], where 55 is obtained from $[(227-11+0)/4+1=55]$.

The computations (e.g., dot product computations) for a convolutional layer, or other layers, of a CNN involve performing mathematical operations, e.g., multiplication and addition, using a computation unit of a hardware circuit of the machine learning model 120. The design of a hardware circuit can cause a system to be limited in its ability to fully utilize computing cells of the circuit when performing computations for layers of a neural network. A more detailed example of an architecture of the machine learning model 120 discussed later with reference to FIG. 5.

While this specification generally describes a patient as a human patient, implementations are not so limited. For example, a patient can refer to a non-human animal, a plant, or a human replica system.

Figure 2:
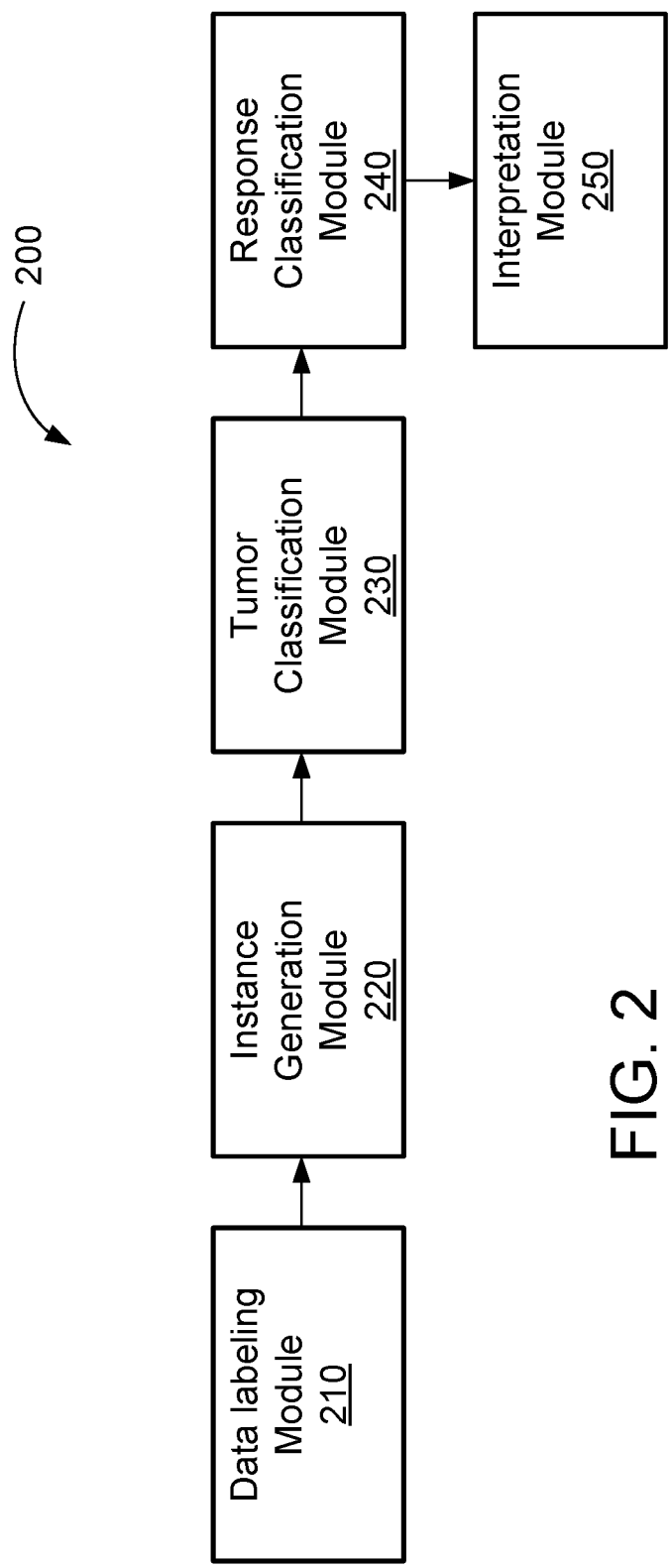
FIG. 2 is a flow diagram illustrating an example architecture of a data processing system.

FIG. 2 is a flow diagram illustrating an architecture of a data processing system 200. The data processing system 200 can be substantially similar to the data processing system 100 described previously with reference to FIG. 1. The data processing system 200 includes a data labeling module 210, an instance generation module 220, a tumor classification module 230, a response classification module 240, and an interpretation module 250. The modules 210-250 can be executed by, for example, the computer processors 110 of the data processing system 100 discussed previously with reference to FIG. 1.

The data labeling module 210 is capable of receiving data representing a plurality of biological images of a patient. The data labeling module 210 facilitates the labeling of the tiles of the images. For example, the labeling module 210 can include a graphical user interface (GUI) that allows a user to manually label a tile to indicate whether or not the tiles include imagery of a cancerous tumor. By facilitating the labeling of the tiles (which is sometimes referred to as weak labeling compared to pixel-wise labeling), the knowledge of the user (e.g., human medical experts) can be incorporated into the data and, therefore, enable training of machine learning models (such as the machine learning model 120 described previously with reference to FIG. 1).

The instance generation module 220 is configured to generate image tile data by segmenting each of the received images into a plurality of image tiles (instances). For example, if an image has dimensions of 4096×4096, the instance generation module 220 can segment the image into 256 tiles (instances) having dimensions of 256×256. Each of the plurality of image tiles can include a discrete portion of a biological image. The number of image tiles generated can be chosen based on computational efficiency, computational power, and computational accuracy considerations. For example, the number of tiles per image can vary from a couple tiles to several thousands of tiles due to the heterogeneities of medical images (e.g., as seen in immunohistochemistry images of biopsy samples from cancer patients).

The tumor classification module 230 can classify each image as "Tumor" or "Non-Tumor" by analyzing the image tiles corresponding to the image. In some implementations, a tumor classification indicates that at least one tile corresponding to the image includes imagery of cancerous tumor cells. In some implementations, a non-tumor classification indicates that no tiles corresponding to the image include imagery of cancerous tumor cells. In some implementations, the tiles can be weighted in accordance with their predictive power associated with the tumor/non-tumor classification. For example, if an image tile of an image includes stronger indications of cancerous cells, that image tile can be assigned a higher weight than the other image tiles of the same image that have weaker indications of cancerous cells (or fail to show indications of cancerous cells.

Figures 3A, 3B:
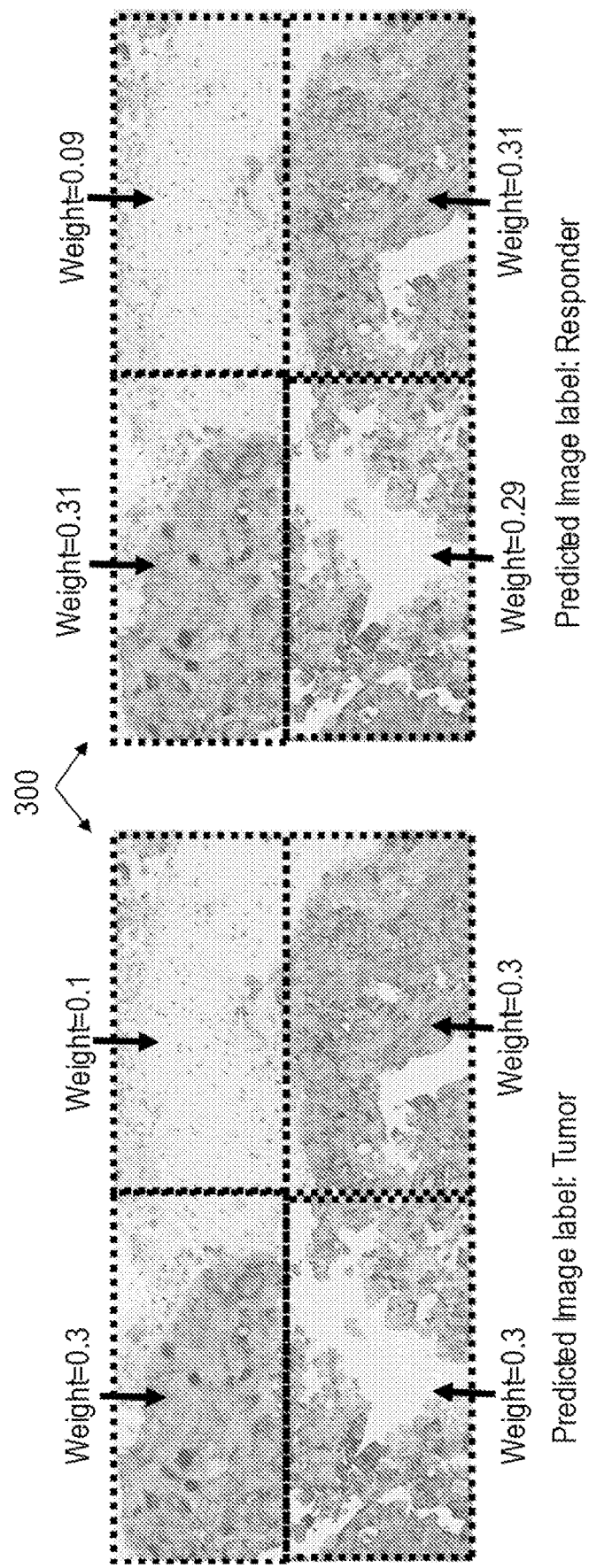
FIGS. 3A-3B illustrate examples of a data processing system labeling an image based on weights assigned to tiles of the image.

FIG. 3A illustrates an example of a data processing system labeling an image 300 as a "Tumor" and assigning weights to the tiles of the image. As shown, the image 300 is segmented into four tiles. The image 300 has been labeled as "Tumor" because at least one image tile includes imagery of cancerous tumor cells. Furthermore, the tiles of image 300 have been assigned weights relative to each other, in which each weight indicates the amount of responsibility the corresponding tile had on the underlying classification. The sum of the weights equals one. As will be explained later, ensuring that the sum of the weights equals one can decrease variance between images.

Referring back to FIG. 2, the response classification module 240 receives each of the images that were labeled as "Tumor," and classifies each of those images as "Responder" or "Non-Responder." In some implementations, a "Responder" classification reflects that the image includes at least one tile that includes imagery indicating that the patient will respond to a chemical substance (e.g., the chemical substance will cause a reduction in the size of a tumor). In some implementations, a "Non-Responder" classification reflects that the image does not include at least one tile including imagery indicating that the patient will not respond to the chemical substance (e.g., the chemical substance will have little to no effect on the size of a tumor). In some implementations, the tiles can be weighted in accordance with their predictive power associated with the Responder/Non-Responder classification. For example, if an image tile of an image includes stronger indications that the patient will respond to a chemical substance, that image tile can be assigned a higher weight than the other image tiles of the same image that have weaker indications that the patient will respond to a chemical substance (or that fail to show indications that the patient will respond to a chemical substance).

FIG. 3B illustrates an example of a data processing system labeling an image 300 as a "Responder" and assigning weights to the tiles of the image 300. As shown, the image 300 has been segmented into 4 tiles. The image 300 has been labeled "Responder" because at least one tile exhibits imagery indicating that the patient will respond to a chemical substance. Furthermore, the tiles of image 300 have been assigned weights relative to each other, in which each weight indicates the amount of responsibility the corresponding tile had on the underlying classification. The sum of the weights equals one. As will be explained later, ensuring that the sum of the weights equals one can decrease variance between images.

Referring back to FIG. 2, the interpretation module 250 receives the weighted image tiles of each image and reconstructs each image. The interpretation module 250 can then determine which portions of the image have triggered the resulting classification of each image by multiplying the weight assigned to a tile with the data matrix of each original tile. The interpretation module 250 can then preprocess the images such that tiles with smaller weights will appear darker than tiles with larger weights and tiles with larger weights will be more prominent in the image. The interpretation module 250 can then aggregate the classification by multiplying the weight of each tile with the prediction from each tile to predict, at the image level, if the patient will respond to the chemical substance. In some implementations, the weighting scheme acts as an attention mechanism that improves the interpretability of the output of a machine learning process.

Although specific modules, including the data labeling module 210, the instance generation module 220, the tumor classification module 230, the response classification module 240, and the interpretation module 250, are described as carrying out certain aspects of the techniques described in this specification, some or all of the techniques may be carried out by additional, fewer, or alternative modules in some implementations.

Figure 4:
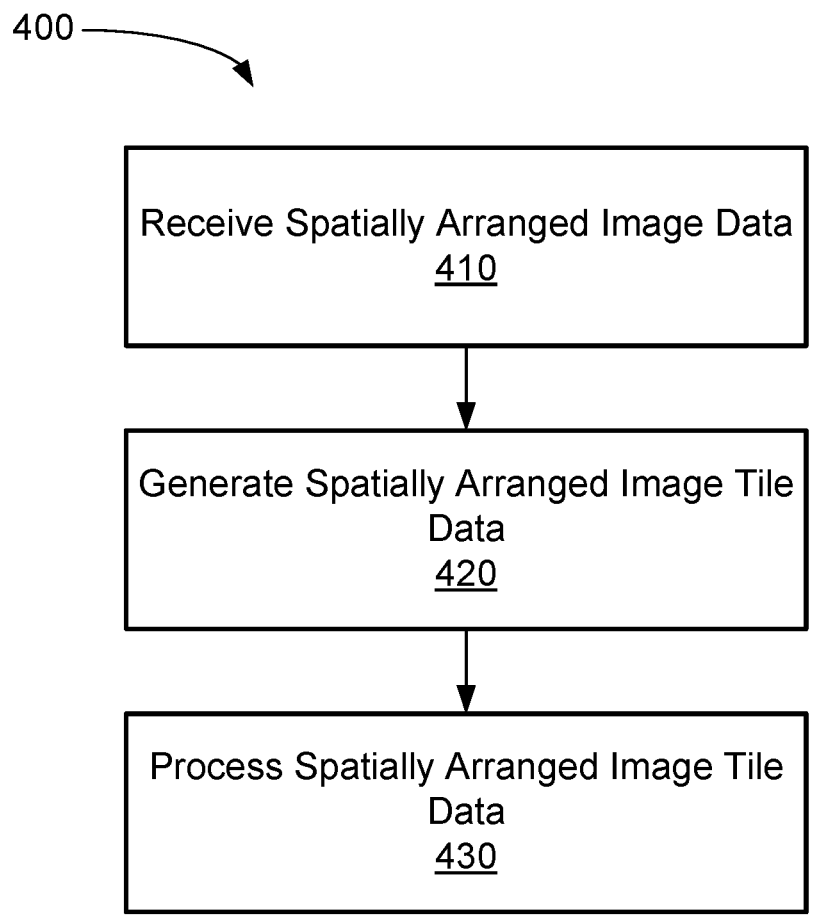
FIG. 4 is a flow chart illustrating an example method for predicting patient response to a chemical compound.

FIG. 4 is a flow chart illustrating an example method 400 for predicting patient response to a chemical compound. The method 400 includes receiving spatially arranged image data (block 410). The spatially arranged image data can represent a plurality of biological images of a patient. For example, as discussed previously with reference to FIG. 1, the biological images can be one or more immunohistochemistry images of the patient's biological tissue.

The method 400 includes generating spatially arranged image tile data (block 420). For example, spatially arranged image tile data can be generated for each image, in which the tile data represents image tiles of the image. Each image tile can include a discrete portion of the corresponding image.

The method 400 includes processing the spatially arranged image tile data (block 430). For example, an artificial neural network can be used to processes the spatially arranged image tile data to predict one or more responses of a patient by analyzing the image tiles. In some implementations, this includes classifying each of the plurality of images as "Tumor" or "Non-Tumor" by analyzing the plurality of image tiles corresponding to the image, as discussed previously with reference to FIGS. 1-2. In some implementations, this includes further classifying each of the images classified as "Tumor" as "Responder" or "Non-Responder," as discussed previously with reference to FIGS. 1-2. The number of images classified as "Responder" can be aggregated with the number of images classified as "Non-Responder" to determine if the patient will respond to a chemical substance.

Figure 5:
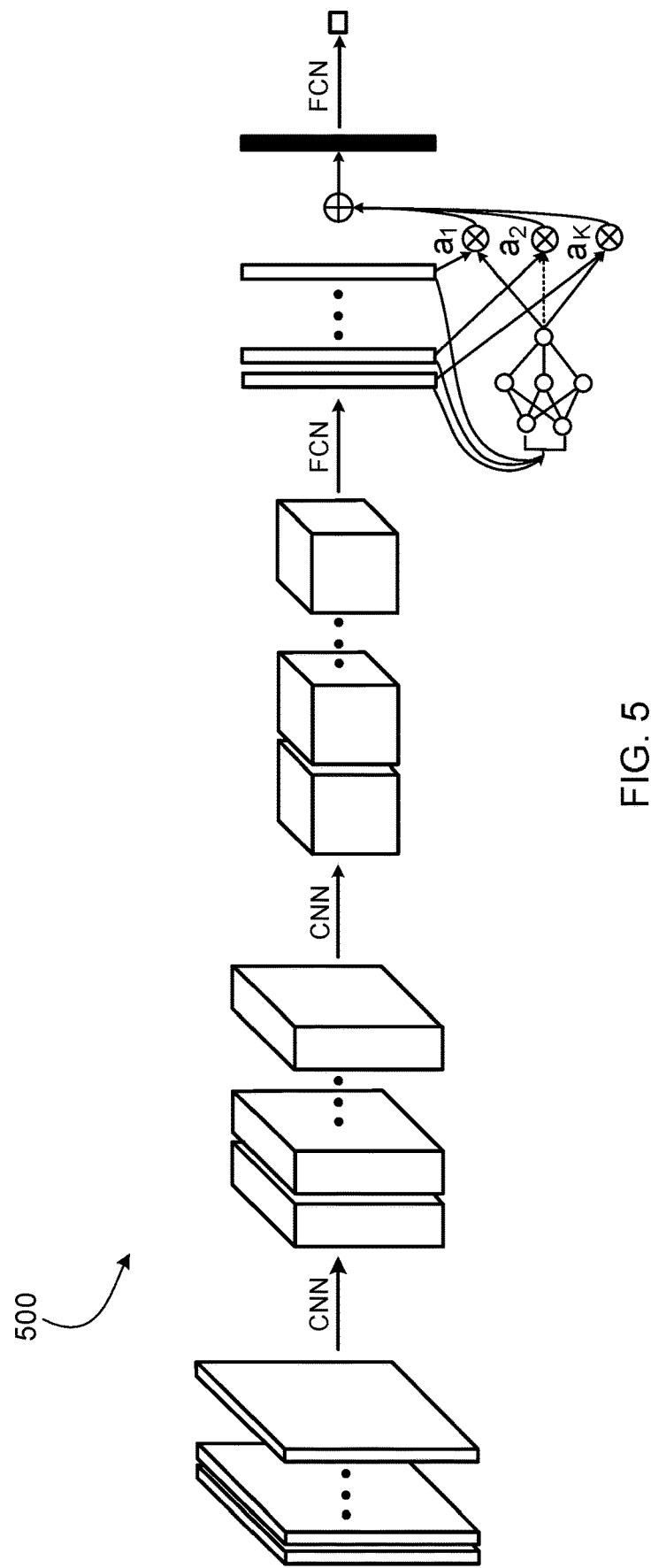
FIG. 5 is a diagram illustrating an example architecture of an artificial neural network.

FIG. 5 is a diagram illustrating an example architecture 500 of an artificial neural network. The architecture 500 can be integrated with the machine learning model 120 described previously with reference to FIG. 1. As shown, the architecture 500 includes one or more convolutional layers ("CNN") and one or more fully connected layers ("FCN"). The architecture 500 may be referred to as an attention-based architecture that utilizes a weighted average of instances (e.g., image tiles), in which the weights are determined by the artificial neural network. In some implementations, the weights sum to 1 to be invariant to the size of a bag (e.g., invariant to the number of tiles of an image). For example, if H={h1, . . . , hk} is the embedding of an image having (k) instances, the architecture can use the following pooling scheme:

$$z = \sum_{k=1}^{K} a_k h_k$$

where:

$$a_k = \frac{\exp\{w^T \tanh(V h_k^T)\}}{\sum_{j=1}^{k} \exp\{w^T \tanh(V h_j^T)\}}$$

where $w \in R^{L \times 1}$ and $V \in R^{L \times M}$ are parameters. The hyperbolic tangent (tanh) is used element-wise non-linearly to include both negative and positive values to facilitate gradient flow. The architecture 500 facilitates the discovery of similarities or dissimilarities among instances (e.g., image tiles). In some implementations, a gated attention mechanism is used according to the following formulation:

$$a_k = \frac{\exp\{w^T(\tanh(V h_k^T) \odot sigm(U h_k^T))\}}{\sum_{j=1}^{k} \exp\{w^T(\tanh(V h_j^T) \odot sigm(U h_j^T))\}}$$

where $U \in R^{L \times M}$ are parameters, $\odot$ is an element-wise multiplication and sigm(.) is the sigmoid non-linearity. The gating mechanism can introduce a learnable non-linearity.

The attention-based architecture can facilitate the assigning of different weights to image tiles within an image, and hence the final representation of the image can be informative of the image level classification. That is, the architecture may find "key" image tiles. By finding these key instances, the architecture 500 can provide regions of interest with a final patient level classification.

Figure 6:
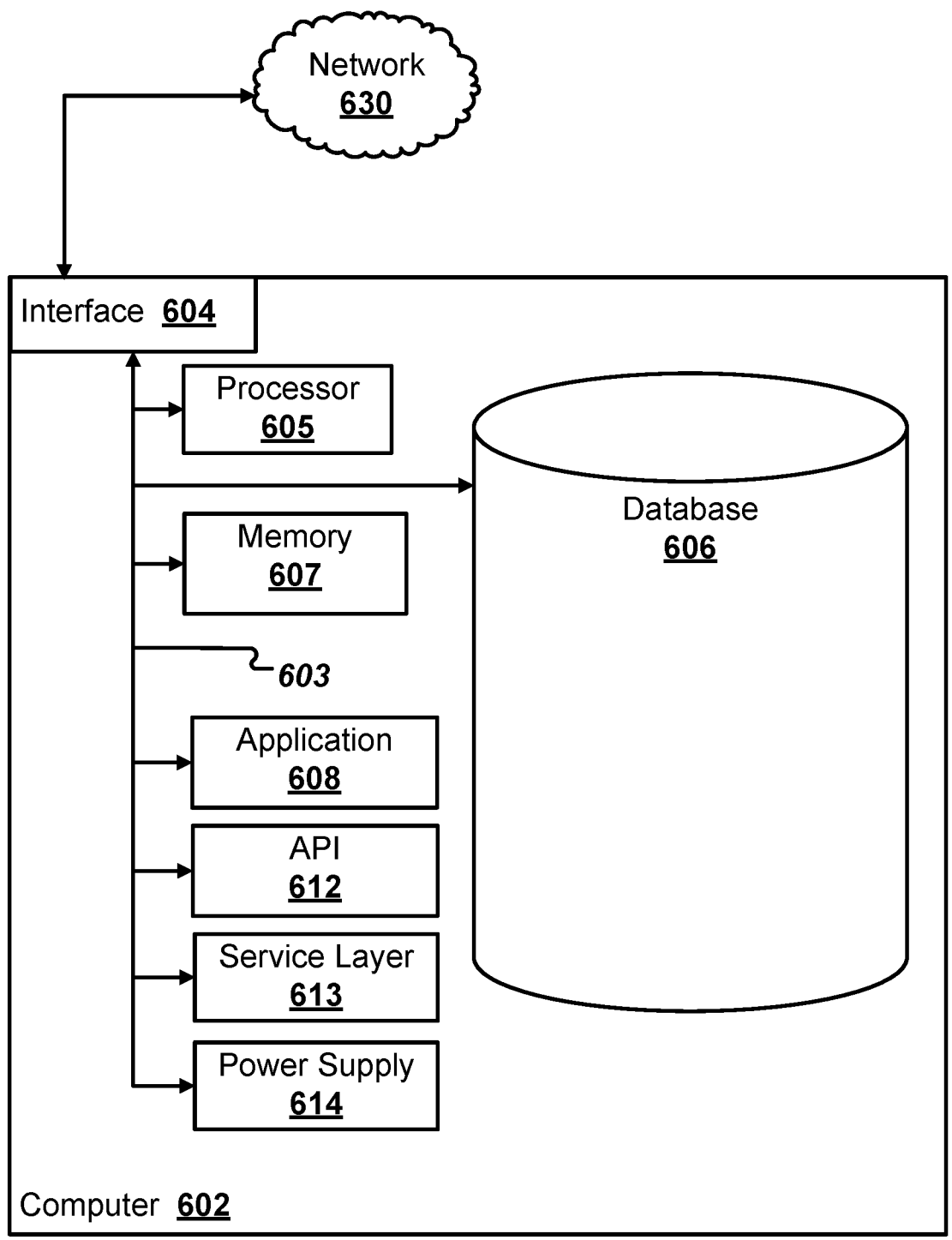
FIG. 6 is a block diagram of an example computer system used to provide computational functionalities associated with described algorithms, methods, functions, processes, flows, and procedures described in the present disclosure.

FIG. 6 is a block diagram of an example computer system 600 used to provide computational functionalities associated with described algorithms, methods, functions, processes, flows, and procedures described in the present disclosure (such as the method 200 described previously with reference to FIG. 2), according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the interface's hardware can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component (for example, as a data server), or that includes a middleware component (for example, an application server). Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

In the foregoing description, implementations have been described with reference to numerous specific details that may vary from implementation to implementation. The description and drawings are, accordingly, to be regarded in an illustrative rather than a restrictive sense. Any definitions expressly set forth herein for terms contained in the claims shall govern the meaning of such terms as used in the claims. In addition, when we use the term "further comprising" or "further including" in the foregoing description or following claims, what follows this phrase can be an additional step or entity, or a sub-step/sub-entity of a previously-recited step or entity.

Figure 7:
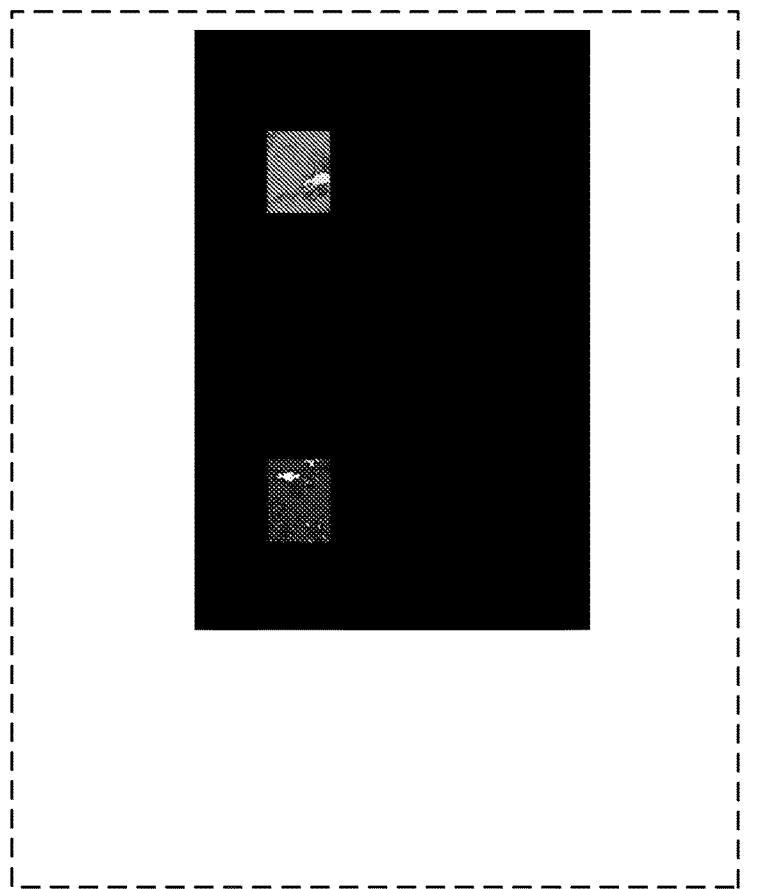
FIG. 7 illustrates an example of an image classified as a responder using the systems and methods described in this specification.
Figure 7:
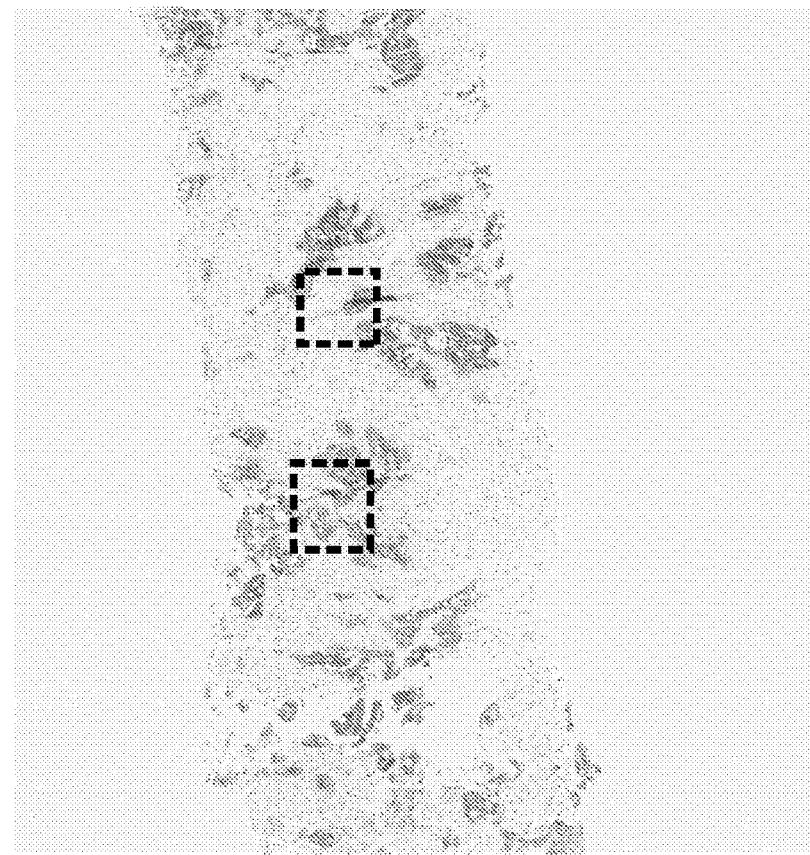

Experimental Results:

FIG. 7 illustrates an example of an image classified as a Responder using the systems and methods described in this specification. As shown, the highlighted regions include interpretable features of tumor cells with drug targeted antigens, and facilitates a correct prediction of being a Responder.

Figure 8:
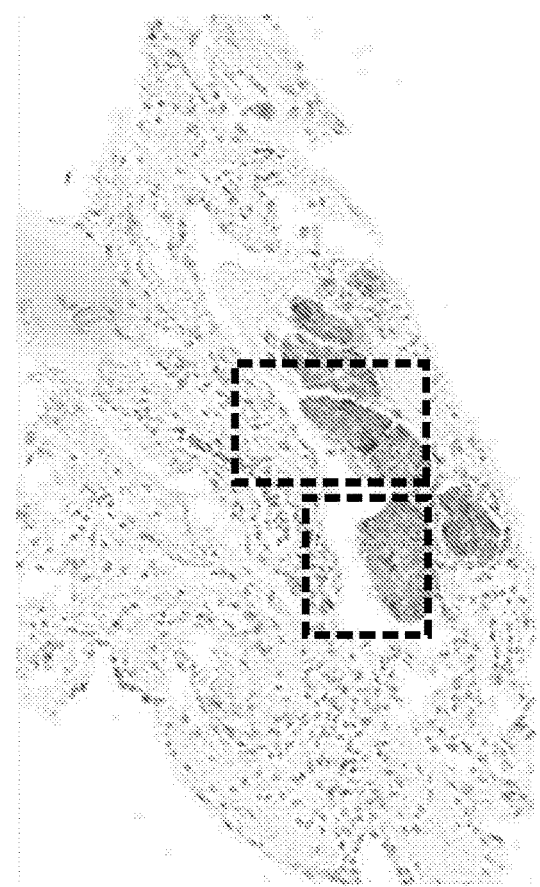
FIG. 8 illustrates an example of an image classified as a non-responder using the systems and methods described in this specification.
Figure 8:
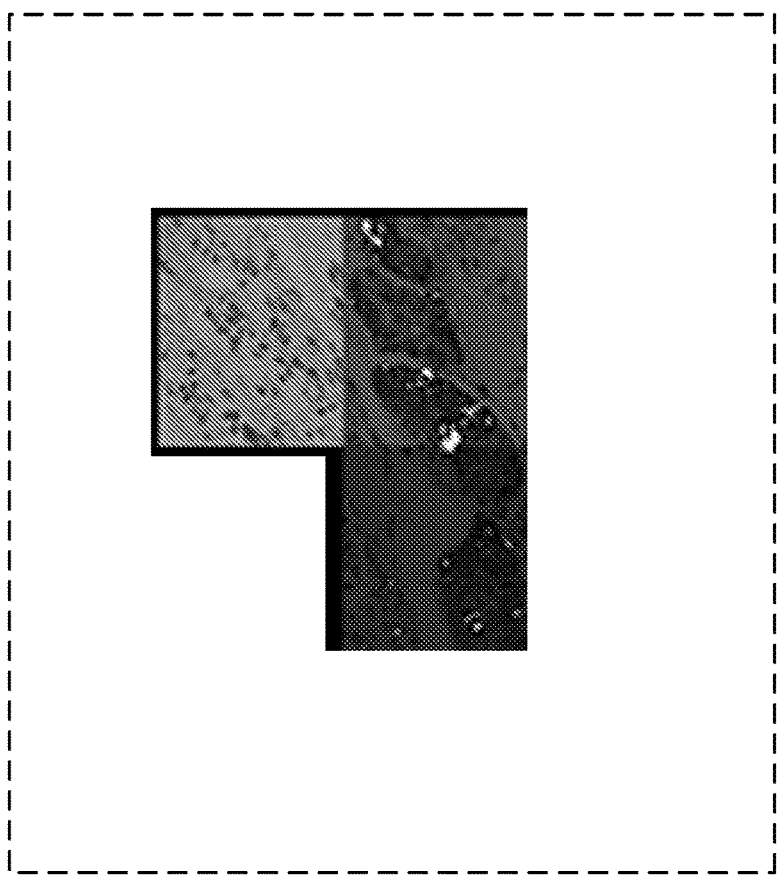

FIG. 8 illustrates an example of an image classified as a Non-Responder using the systems and methods described in this specification. As shown, the highlighted region includes tumor nests with antigen patterns associated with Non-Responder classifications. The use of the weighting (attention) mechanism allows human medical experts to meaningfully interpret the results, which can increase the trustworthiness of the machine learning model.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. Nevertheless, it will be understood that various modifications may be made without departing from the spirit and scope of this disclosure.

What is claimed is:

1. A system comprising:
   one or more computers; and
   one or more storage devices communicatively coupled to the one or more computers, wherein the one or more storage devices store instructions that, when executed by the one or more computers, cause the one or more computers to perform operations comprising:
      receiving spatially arranged image data representing a biological image of a patient;
      generating spatially arranged image tile data representing a plurality of image tiles, wherein each image tile of the plurality of image tiles comprises a discrete portion of the biological image;
      processing the spatially arranged image tile data using an artificial neural network and in accordance with trained values of a set of artificial neural network parameters, wherein the artificial neural network performs operations comprising:
         generating, by the artificial neural network and for each of the plurality of image tiles, a response score characterizing whether the patient will respond to a chemical substance;
         generating, by the artificial neural network and for each of the plurality of image tiles, a response weight that indicates a predictive power of the image tile in predicting whether the patient will respond to the chemical substance; and
      generating an overall response score defining a predicted response of the patient to the chemical substance by combining the response scores for the plurality of image tiles with the response weights for the plurality of image tiles;
      identifying, based on the response weights, a subset of the plurality of image tiles having highest response weights as key image tiles that contributed most significantly to predicting the overall response score; and
      outputting: (i) the overall response score defining the predicted response of the patient to the chemical substance, and (ii) a visual rendering that highlights the key image tiles in the biological image.

2. The system of claim 1, wherein the artificial neural network comprises at least one convolutional layer and at least one fully connected layer.

3. The system of claim 1, wherein the biological image is an immunohistochemistry image.

4. A method performed by one or more computers, the method comprising:
   receiving spatially arranged image data representing a biological image of a patient;
   generating spatially arranged image tile data representing a plurality of image tiles, wherein each image tile of the plurality of image tiles comprises a discrete portion of the biological image;
   processing the spatially arranged image tile data using an artificial neural network and in accordance with trained values of a set of artificial neural network parameters, wherein the artificial neural network performs operations comprising:
      generating, by the artificial neural network and for each of the plurality of image tiles, a response score characterizing whether the patient will respond to a chemical substance;
      generating, by the artificial neural network and for each of the plurality of image tiles, a response weight that indicates a predictive power of the image tile in predicting whether the patient will respond to the chemical substance; and
   generating an overall response score defining a predicted response of the patient to the chemical substance by combining the response scores for the plurality of image tiles with the response weights for the plurality of image tiles;
   identifying, based on the response weights, a subset of the plurality of image tiles having highest response weights as key image tiles that contributed most significantly to predicting the overall response score; and
   outputting: (i) the overall response score defining the predicted response of the patient to the chemical substance, and (ii) a visual rendering that highlights the key image tiles in the biological image.

5. The method of claim 4, wherein the biological image is an immunohistochemistry image.

6. One or more non-transitory computer storage media encoded with computer program instructions that when executed by one or more computers cause the one or more computers to perform operations comprising:
   receiving spatially arranged image data representing a biological image of a patient;
      generating spatially arranged image tile data representing a plurality of image tiles, wherein each image tile of the plurality of image tiles comprises a discrete portion of the biological image;
      processing the spatially arranged image tile data using an artificial neural network and in accordance with trained values of a set of artificial neural network parameters, wherein the artificial neural network performs operations comprising:
         generating, by the artificial neural network and for each of the plurality of image tiles, a response score characterizing whether the patient will respond to a chemical substance;
         generating, by the artificial neural network and for each of the plurality of image tiles, a response weight that indicates a predictive power of the image tile in predicting whether the patient will respond to the chemical substance; and generating an overall response score defining a predicted response of the patient to the chemical substance by combining the response scores for the plurality of image tiles with the response weights for the plurality of image tiles;

identifying, based on the response weights, a subset of the plurality of image tiles having highest response weights as key image tiles that contributed most significantly to predicting the overall response score; and outputting: (i) the overall response score defining the predicted response of the patient to the chemical substance, and (ii) a visual rendering that highlights the key image tiles in the biological image.

7. The non-transitory computer storage media of claim 6, wherein the biological image is an immunohistochemistry image.

8. The system of claim 1, wherein generating an overall response score defining a predicted response of the patient to the chemical substance by combining the response scores for the plurality of image tiles with the response weights for the plurality of image tiles comprises:

generating, for image of the plurality of image tiles, a tile-level response score for the image tile as a product of the response score for the image tile and the response weight for the image tile; and generating the overall response score by summing the tile-level response scores for the plurality of image tiles.

9. The system of claim 1, wherein the overall response score defines a cardiovascular risk resulting from the patient undergoing an oncology drug treatment that comprises the chemical substance.

10. The system of claim 1, wherein the overall response score defines a change in tumor size that is predicted to result from administering the chemical substance to the patient.

11. The system of claim 1, wherein the overall response score defines a predicted toxicity of the chemical substance to the patient.

12. The system of claim 1, wherein the overall response score characterizes whether the patient will experience an adverse reaction from being administered the chemical substance.

13. The system of claim 1, wherein generating, by the artificial neural network and for each of the plurality of image tiles, a response weight that indicates a predictive power of the image tile in predicting whether the patient will respond to a chemical substance comprises:

generating the response weights under a constraint that a sum of the response weights across the plurality of image tiles is equal to a predefined value.

14. The system of claim 13, wherein the predefined value is one.

15. The system of claim 1, wherein the chemical substance comprises a pharmaceutical drug.

16. The system of claim 1, further comprising, prior to generating the overall response score for the patient:

receiving a plurality of input biological images of the patient;

classifying, using a second artificial neural network, a subset of the plurality of input biological images as being abnormal biological images that display abnormal tissue;

wherein the overall response score for the patient is generated based only on the subset of the plurality of input biological images that are classified as being abnormal biological images that display abnormal tissue.

17. The system of claim 16, wherein abnormal tissue comprises cancerous tissue.

18. The system of claim 16, wherein classifying, using the second artificial neural network, the subset of the plurality of input biological images as being abnormal biological images that display abnormal tissue comprises, for each of the plurality of input biological images:

generating, by the second artificial neural network and for each of a plurality of input image tiles included in the input biological image, an abnormality score characterizing whether the input image tile shows abnormal tissue; and classifying whether the input biological image is an abnormal biological image based on the abnormality scores.

19. The system of claim 18, wherein classifying whether the input biological image is an abnormal biological image based on the abnormality scores comprises:

classifying the input biological image as an abnormal biological image if the abnormality scores for the input image tiles of the input biological image indicate that at least one input image tile shows abnormal tissue.

20. The system of claim 1, wherein the artificial neural network implements a gated attention mechanism.

\* \* \* \* \*